United States Patent
Hashimoto et al.

(10) Patent No.: US 10,166,154 B2
(45) Date of Patent: Jan. 1, 2019

(54) SHAPED NON-WOVEN FABRIC FOR ABSORBENT ARTICLE, ABSORBENT ARTICLE INCLUDING SAID SHAPED NON-WOVEN FABRIC, AND METHOD FOR MANUFACTURING SAID SHAPED NON-WOVEN FABRIC

(71) Applicant: UNICHARM CORPORATION, Ehime (JP)

(72) Inventors: Tatsuya Hashimoto, Kagawa (JP); Tetsuo Okubo, Kagawa (JP); Huanhuan Chen, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/741,189

(22) PCT Filed: Mar. 18, 2016

(86) PCT No.: PCT/JP2016/058857
§ 371 (c)(1),
(2) Date: Dec. 29, 2017

(87) PCT Pub. No.: WO2017/002409
PCT Pub. Date: Jan. 5, 2017

(65) Prior Publication Data
US 2018/0193208 A1   Jul. 12, 2018

(30) Foreign Application Priority Data
Jun. 30, 2015   (JP) ................................ 2015-132129

(51) Int. Cl.
*A61F 13/15* (2006.01)
*A61F 13/513* (2006.01)
(Continued)

(52) U.S. Cl.
CPC ............ *A61F 13/513* (2013.01); *A61F 13/15* (2013.01); *A61F 13/15203* (2013.01);
(Continued)

(58) Field of Classification Search
None
See application file for complete search history.

(56) References Cited

U.S. PATENT DOCUMENTS

| | | | | |
|---|---|---|---|---|
| 5,807,363 | A | * | 9/1998 | Hamajima .......... A61F 13/4752 604/366 |
| 2007/0298213 | A1 | | 12/2007 | Noda et al. |
| 2010/0178456 | A1 | | 7/2010 | Kuroda et al. |

FOREIGN PATENT DOCUMENTS

| | | |
|---|---|---|
| JP | 01-256955 A | 10/1989 |
| JP | 04-058951 A | 2/1992 |

(Continued)

OTHER PUBLICATIONS

International Search Report issued in PCT/JP2016/058857, dated Jun. 7, 2016, 5 pages.

*Primary Examiner* — Jacqueline Stephens
(74) *Attorney, Agent, or Firm* — Hauptman Ham, LLP

(57) ABSTRACT

A shaped non-woven fabric for an absorbent has a first surface and a second surface and is usable with the second surface facing a constituent member of an absorbent article. The shaped non-woven fabric is includes a thermoplastic resin fiber. The non-woven fabric includes a plurality of first recesses which have openings in the first surface and are recessed toward the second surface, and a plurality of through-holes which penetrate from the first surface to the second surface. Each of the plurality of first recesses has a peripheral wall section which extends in the thickness direction from the end edges of the openings toward the second surface, and a bottom section connected to the end edge of the peripheral wall section. At least a portion of the (Continued)

plurality of first recesses includes a hole section which penetrates from the first surface to the second surface.

9 Claims, 9 Drawing Sheets

(51) Int. Cl.
| | |
|---|---|
| *A61F 13/51* | (2006.01) |
| *A61F 13/511* | (2006.01) |
| *A61F 13/512* | (2006.01) |
| *B29C 59/04* | (2006.01) |
| *B29K 101/12* | (2006.01) |
| *B29K 105/00* | (2006.01) |
| *B29L 31/48* | (2006.01) |

(52) U.S. Cl.
CPC ........ *A61F 13/15707* (2013.01); *A61F 13/51* (2013.01); *A61F 13/511* (2013.01); *A61F 13/512* (2013.01); *A61F 13/5126* (2013.01); *A61F 13/51108* (2013.01); *A61F 2013/15406* (2013.01); *A61F 2013/15552* (2013.01); *A61F 2013/15715* (2013.01); *A61F 2013/51009* (2013.01); *A61F 2013/51026* (2013.01); *A61F 2013/51338* (2013.01); *B29C 59/04* (2013.01); *B29K 2101/12* (2013.01); *B29K 2105/256* (2013.01); *B29L 2031/4878* (2013.01)

(56) References Cited

FOREIGN PATENT DOCUMENTS

| | | |
|---|---|---|
| JP | 08-302555 A | 11/1996 |
| JP | 2003-116909 A | 4/2003 |
| JP | 2007-216034 A | 8/2007 |
| JP | 2008-025084 A | 2/2008 |
| JP | 2014-519421 A | 8/2014 |
| WO | 2008/146541 A1 | 12/2008 |
| WO | 2012/148936 A1 | 11/2012 |

* cited by examiner

SHAPED NON-WOVEN FABRIC FOR ABSORBENT ARTICLE, ABSORBENT ARTICLE INCLUDING SAID SHAPED NON-WOVEN FABRIC, AND METHOD FOR MANUFACTURING SAID SHAPED NON-WOVEN FABRIC

RELATED APPLICATIONS

The present application is a National Phase of International Application Number PCT/JP2016/058857, filed Mar. 18, 2016, and claims priority to Japanese Application Number 2015-132129, filed Jun. 30, 2015.

TECHNICAL FIELD

The present invention relates to a nonwoven fabric which is shaped to be used for an absorbent article, an absorbent article which includes the shaped nonwoven fabric, and a manufacturing method of the shaped nonwoven fabric.

Nonwoven fabrics which are manufactured by processing nonwoven fabrics and have various properties have been provided.

For example, in Patent Literature 1, a top sheet of an absorbent article in which various physical properties required for the top sheet of the absorbent article, such as the fitting property, the texture, the dry feeling, the soft feeling, etc., are improved has been described.

The top sheet of Patent Literature 1 is a top sheet for an absorbent article formed by a nonwoven fabric, in which a large number of ridge portions and groove portions are alternately arranged so as not to have a planar portion, each of the ridge portions is curved in a protruded manner and each of the groove portions is curved in a recessed manner, and the groove portions include a large number of openings disposed with intervals, characterized in that, the ratio (MD/CD) of the bulk softness in the direction (MD) which is parallel to the ridge portions and the groove portions to the bulk softness in the direction (CD) which is perpendicular to the ridge portions and the groove portions is 1.7 or more, the bulk softness in the CD direction is 12 g or less, and the thickness "d" under 0.5 g/cm$^2$ load is 0.7 mm or more.

CITATION LIST

Patent Literature

PTL 1: Japanese Unexamined Patent Publication No. H8-302555

SUMMARY OF INVENTION

Technical Problem

However, the top sheet described in Patent Literature 1 is manufactured by heating the pin roll to a high temperature and partially softening or partially melting the nonwoven fabric contacting the protruded pin peripheral portion by heat, whereby the lower peripheral portion of the nonwoven fabric tends to be hardened, and tends to be inferior in the texture thereof. Further, in the top sheet described in Patent Literature 1, the ventilation passage in the planar direction formed by the ridge portions curved in the protruded manner and the ventilation passage in the thickness direction formed by the openings do not communicate with each other except for the gaps in the nonwoven fabric which configures the top sheet, whereby it is difficult for the air with high humidity, etc., which has moved in the planar direction on the back surface side of the top sheet to move to the front surface side of the top sheet and thus the top sheet described in Patent Literature 1 is inferior in air permeability in the thickness direction.

Incidentally, although the top sheet described in Patent Literature 1 includes the openings which open in the thickness direction, the openings are opened in the thickness direction of the top sheet, and the lower peripheral portions of the openings form the bottom surface of the top sheet, whereby it is difficult for the air in the back surface of the top sheet in which the openings are not present to move to the front surface of the top sheet.

As described above, the object of the present disclosure is to provide a nonwoven fabric which is shaped to be used for an absorbent article, having excellent, texture and excellent air permeability in the thickness direction due to ease of the air on one surface side moving to the other surface side.

Solution to Problem

The present inventors have found that a nonwoven fabric which is shaped to be used for an absorbent article, including a first surface, a second surface which is positioned on an opposite side of the first surface, and a thickness direction, and is used in a state in which the second surface faces a configuration member of the absorbent article, wherein the nonwoven fabric includes a thermoplastic resin fiber, the nonwoven fabric includes a plurality of recessed portions each having an aperture portion on the first surface and each being dented toward a second surface side, and a plurality of penetration holes each being provided in a region other than the recessed portions and each penetrating through from the first surface to the second surface, each of the plurality of recessed portions includes a circumferential wall portion which extends in the thickness direction from an edge of the aperture portion toward the second surface side, and a bottom portion which is connected to an edge of the circumferential wall portion, the edge of the circumferential wall portion being positioned on an opposite side of the aperture portion, and at least a part of the plurality of recessed portions includes a hole portion which penetrates through the circumferential wall portion from the first surface to the second surface, in the circumferential wall portion is the solution to the problem.

Advantageous Effects of Invention

The nonwoven fabric which is shaped to be used for an absorbent article of the present disclosure has an excellent texture and excellent air permeability in the thickness direction due to ease of the air on one surface side moving to the other surface side.

DESCRIPTION OF EMBODIMENTS

Figure 1:
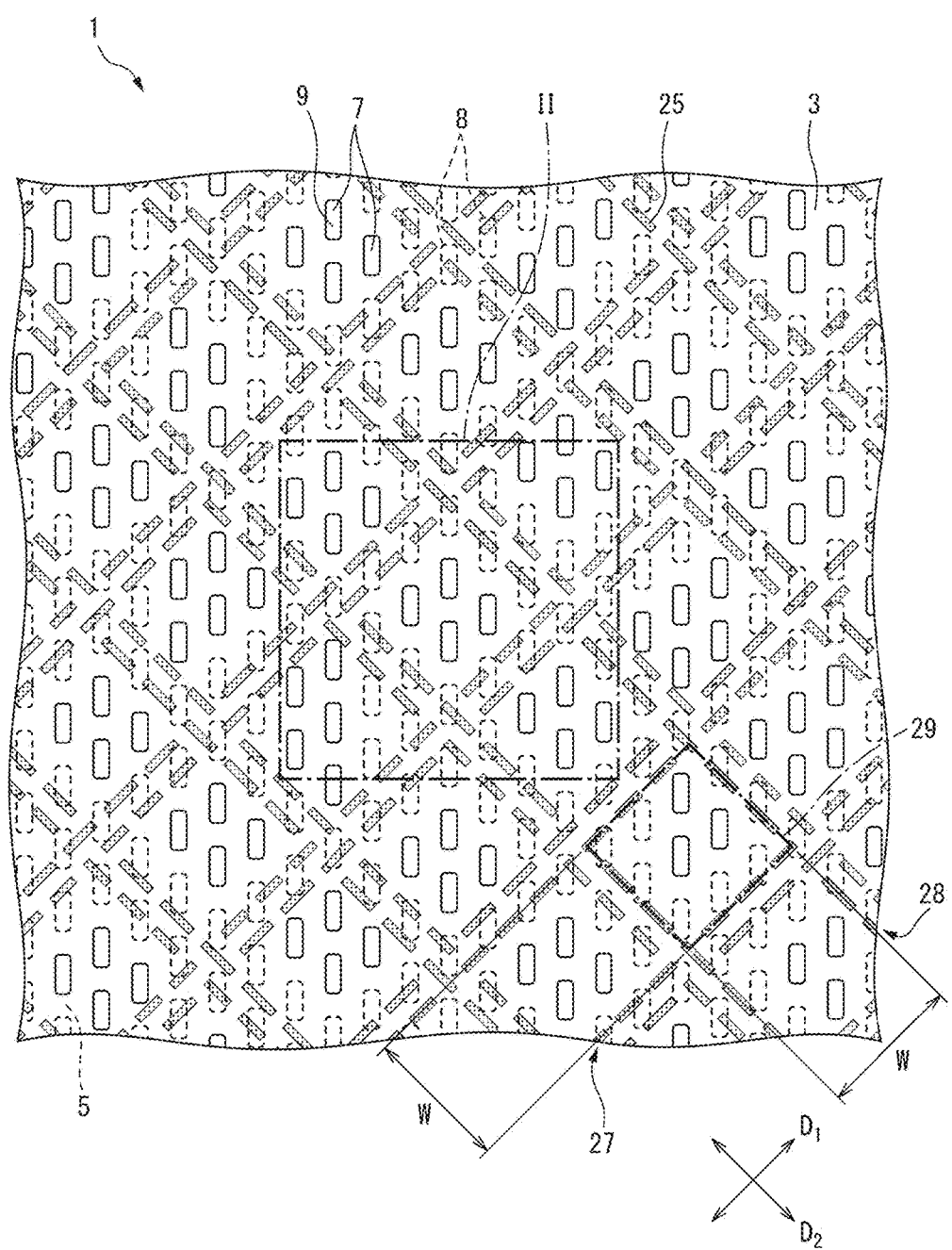
FIG. 1 is a planar view of the shaped nonwoven fabric 1 according to the first embodiment.

The present disclosure relates to the following aspects.

Incidentally, in the present description, the nonwoven fabric which is shaped to be used for an absorbent article may be referred to simply as the shaped nonwoven fabric.

[Aspect 1]

A nonwoven fabric which is shaped to be used for an absorbent article, including a first surface, a second surface which is positioned on an opposite side of the first surface, and a thickness direction, and being used in a state in which the second surface faces a configuration member of the absorbent article, wherein the nonwoven fabric includes a thermoplastic resin fiber, the nonwoven fabric includes a plurality of recessed portions each having an aperture portion on the first surface and each being dented toward a second surface side, and a plurality of penetration holes each being provided in a region other than the recessed portions and each penetrating through from the first surface to the second surface, each of the plurality of recessed portions includes a circumferential wall portion which extends in the thickness direction from an edge of the aperture portion toward the second surface side, and a bottom portion which is connected to an edge of the circumferential wall portion, the edge of the circumferential wall portion being positioned on an opposite side of the aperture portion, and at least a part of the plurality of recessed portions includes a hole portion which penetrates through the circumferential wall portion from the first surface to the second surface, in the circumferential wall portion.

The shaped nonwoven fabric described aspect 1 includes the plurality of recessed portions each being dented toward the second surface side, and the circumferential wall portion of the recessed portions includes the hole portion. Accordingly the recessed portions are superior in the softness, and the shaped nonwoven fabric improves the texture of the first surface.

Further, the shaped nonwoven fabric described in aspect 1 includes the plurality of recessed portions each being dented toward the second surface side, whereby on the second surface side, the region other than the recessed portions form the ventilation passage in the planar direction, and the shaped nonwoven fabric is superior in the air permeability in the planar direction. Further, the above mentioned shaped nonwoven fabric includes the plurality of penetration holes and the hole portion formed in the circumferential wall portion of at least a part of the plurality of recessed portions, and these form the ventilation passage in the thickness direction which communicate with the ventilation passage in the planar direction, whereby the shaped nonwoven fabric is superior in the air permeability in the thickness direction due to ease of the air on one surface side moving to the other surface side.

Accordingly, the shaped nonwoven fabric described in aspect 1 has the advantages of excellent texture and excellent air permeability in the thickness direction due to ease of the air on one surface side moving to the other surface side.

Further, in the case in which the shaped nonwoven fabric described in aspect 1 is used for an absorbent article, a ventilation passage in the planar direction is formed in between the materials of the absorbent article and in the region other than the recessed portions. Further, the shaped nonwoven fabric includes the plurality of penetration holes and the hole portion formed in the circumferential wall portion of at least a part of the plurality of recessed portions, and these form the ventilation passage in the thickness direction which communicate with the ventilation passage in the planar direction. As a result, the air with high humidity inside the absorbent article can move in the planar direction of the shaped nonwoven fabric by passing through the ventilation passage in the planar direction. Further, the air with high humidity which has moved in the planar direction can move to the outside of the absorbent article by passing through the ventilation passage in the thickness direction. Accordingly, the absorbent article which includes the shaped nonwoven fabric described in aspect 1 has an excellent texture and excellent air permeability in the thickness direction due to ease of the air on one surface side (which the material side of the absorbent article) moving to the other surface side (which is the outside of the absorbent article).

[Aspect 2]

The nonwoven fabric according to aspect 1, wherein a partially ruptured portion which is formed by a part of the nonwoven fabric and a part of which being connected to the nonwoven fabric, is dented toward the second surface side, in each of the plurality of penetration holes.

In the shaped nonwoven fabric described in aspect 2, the partially ruptured portion which is formed by a part of the shaped nonwoven fabric is dented toward the second surface side of the shaped nonwoven fabric, whereby the penetration holes are formed. As a result, the above described ventilation passage in the planar direction and the ventilation passage in the thickness direction are to be reliably communicated. Further, since the partially ruptured portion is dented toward the second surface side, the shaped nonwoven fabric described in aspect 2 is superior in the texture in the first surface.

Accordingly, the shaped nonwoven fabric described in aspect 2 has an excellent texture and excellent air permeability in the thickness direction due to ease of the air on one surface side moving to the other surface side.

Further, in the case in which the shaped nonwoven fabric described in aspect 2 is used for an absorbent article, it becomes easier for the air with high humidity to move to the outside of the absorbent article by passing through the ventilation passage in the thickness direction which reliably communicates with the ventilation passage in the planar direction. Accordingly, the absorbent article which includes the shaped nonwoven fabric described in aspect 2 has an excellent texture and excellent, air permeability in the thickness direction due to ease of the air on one surface side (which is the material side of the absorbent article) moving to the other surface side (which is the outside of the absorbent article.).

[Aspect 3]

The nonwoven fabric according to aspect 2, wherein the nonwoven fabric includes a plurality of fusion portions in which the thermoplastic resin fiber is fused, in the region other than the plurality of recessed portions, and an end portion of the partially ruptured portion includes a part of the plurality of fusion portions, at least in a part of the plurality of penetration holes.

The shaped nonwoven fabric described in aspect 3 includes the fusion portions in the region other than the recessed portions, and the end portion of the partially ruptured portion includes a part of the fusion portions. As a result, it becomes difficult for the end portion of the partially ruptured portion to be fuzzy, whereby the first surface is superior in the texture. Accordingly, the shaped nonwoven fabric described in aspect 3, and the absorbent article, which includes such a nonwoven fabric, have an improved texture.

[Aspect 4]

The nonwoven fabric according to aspect 3, wherein at least one of the plurality of recessed portions is disposed on an inside of a compartmented region which is compartmented by a fusion region in which the plurality of fusion portions are continuously or intermittently disposed.

In the shaped nonwoven fabric described in aspect 4, the recessed portion is disposed on the inside of a compartmented region which is compartmented by the fusion region, whereby the ventilation passage in the planar direction is secured by the recessed portion, and the ventilation passage in the thickness direction is secured by the penetration holes formed on the compartmented region. Accordingly, the shaped nonwoven fabric described in aspect 4 has excellent air permeability in the thickness direction due to ease of the air on one surface side moving to the other surface side.

Further, in the case in which the shaped nonwoven fabric described in aspect 4 is used for an absorbent article, it becomes easier for the air with high humidity to move to the outside of the absorbent article by passing through the ventilation passage in the planar direction and the ventilation passage in the thickness direction. Accordingly, the absorbent article which includes the shaped nonwoven fabric described in aspect 4 has excellent air permeability in the thickness direction due to ease of the air on one surface side (which is the material side of the absorbent article 1) moving to the other surface side (which is the outside of the absorbent article).

[Aspect 5]

The nonwoven fabric according to any one of aspects 1 to 4, wherein the hole portion includes a peripheral portion which is formed without being fused with the thermoplastic resin fiber.

In the shaped nonwoven fabric described in aspect 5, and in the absorbent article, which includes such a nonwoven fabric, the hole portion includes the peripheral portion which is formed without being fused with the thermoplastic resin fiber, whereby the shaped nonwoven fabric described in aspect 5, and the absorbent article, which includes such a nonwoven fabric, have an excellent texture.

[Aspect 6]

The nonwoven fabric according to any one of aspects 1 to 5, wherein the thermoplastic resin fiber includes a filament.

The shaped nonwoven fabric described in aspect 6, and the absorbent article including the same, have an excellent texture.

[Aspect 7]

The nonwoven fabric according to any one of aspects 1 to 6, wherein the thermoplastic resin fiber includes a crimped fiber.

The shaped nonwoven fabric described in aspect 7 includes the crimped fiber, whereby even when a force is applied to the shaped nonwoven fabric it is easy for the shaped nonwoven fabric to maintain the shape thereof. As a result, it is easy for the above described ventilation passage in the planar direction and the ventilation passage in the thickness direction to be secured. Accordingly, the shaped nonwoven fabric described in aspect 7 has excellent air permeability in the thickness direction due to ease of the air on one surface side moving to the other surface side.

Further, in the absorbent article which includes the shaped nonwoven fabric described in aspect 7, even when a body pressure, etc, is applied thereto, it is easy for the shaped nonwoven fabric to maintain the shape thereof. Accordingly, the absorbent article which includes the shaped nonwoven fabric described in aspect 7 has excellent air permeability in the thickness direction due to ease of the air on one surface side (which is the material side of the absorbent article) moving to the other surface side (which is the outside of the absorbent article).

[Aspect 8]

The nonwoven fabric according to any one of aspects 1 to 7, wherein the nonwoven fabric is a spunbond nonwoven fabric or a laminated nonwoven fabric of a spunbond nonwoven fabric and a meltblown nonwoven fabric.

The shaped nonwoven fabric described in aspect 8 is formed by the specific nonwoven fabric, whereby is superior in economic efficiency. Further, the above described specific nonwoven fabric is formed by the filament, and the fiber is thin, whereby has an excellent texture.

[Aspect 9]

The absorbent article which includes a liquid permeable sheet, a liquid impermeable sheet, and an absorbent body positioned between the liquid permeable sheet and the liquid impermeable sheet, wherein the liquid permeable sheet is the nonwoven fabric according to any one of aspects 1 to 8, and the second surface of the nonwoven fabric faces the absorbent body.

In the absorbent article described in aspect 9, the ventilation passage in the planar direction is formed in between the materials of the absorbent article and in the region other than the recessed portions. Further, the shaped nonwoven fabric includes the plurality of penetration holes and the hole portion formed in the circumferential wall portion of at least a part of the plurality of recessed portions, and these form the ventilation passage in the thickness direction which communicate with the ventilation passage in the planar direction. As a result, the air with high humidity inside the absorbent article can move in the planar direction of the shaped nonwoven fabric by passing through the ventilation passage in the planar direction. Further, the air with high humidity which has moved in the planar direction can move to the outside of the absorbent article by passing through the ventilation passage in the thickness direction. Accordingly, the absorbent article described in aspect 9 has an excellent texture and excellent air permeability in the thickness direction due to ease of the air on one surface side (which is the material side of the absorbent article) moving to the other surface side (which is the outside of the absorbent article).

[Aspect 10]

The absorbent article which includes a liquid permeable sheet, a liquid impermeable sheet, an absorbent body positioned between the liquid permeable sheet and the liquid impermeable sheet, and an exterior sheet disposed on a surface of the liquid impermeable sheet that is on an opposite side of the absorbent body, wherein the exterior sheet is the nonwoven fabric according to any one of aspects 1 to 8, and the second surface of the nonwoven fabric faces the liquid impermeable sheet.

The absorbent article described in aspect 10 is superior in the texture.

[Aspect 11]

A manufacturing method of the nonwoven fabric according to any one of claims 1 to 8, including:

a step of preheating the nonwoven fabric to be shaped which includes the first surface and the second surface, and further includes the thermoplastic resin fiber, and a step of forming a shaped nonwoven fabric by making the preheated nonwoven fabric to be shaped pass through between a pair of shaping members which include a first shaping member and a second shaping member so that the first surface and the second surface come in contact with the second shaping member and the first shaping member, respectively, and so as to shape the nonwoven fabric to be shaped, wherein In the pair of shaping members, the first shaping member includes a plurality of ridges which extend in one direction and a plurality of grooves each being disposed between the plurality of ridges, and the second shaping member includes a plurality of pins each of which having a tip portion that is disposed intermittently along the one direction and is disposed so as to engage with each of the plurality of grooves.

The shaped nonwoven fabric manufactured by the method described in aspect 11 has the above described effects.

<The Shaped Nonwoven Fabric for an Absorbent Article>

First, the shaped nonwoven fabric for an absorbent article of the present disclosure is described with reference to the drawings as appropriate.

Figure 2:
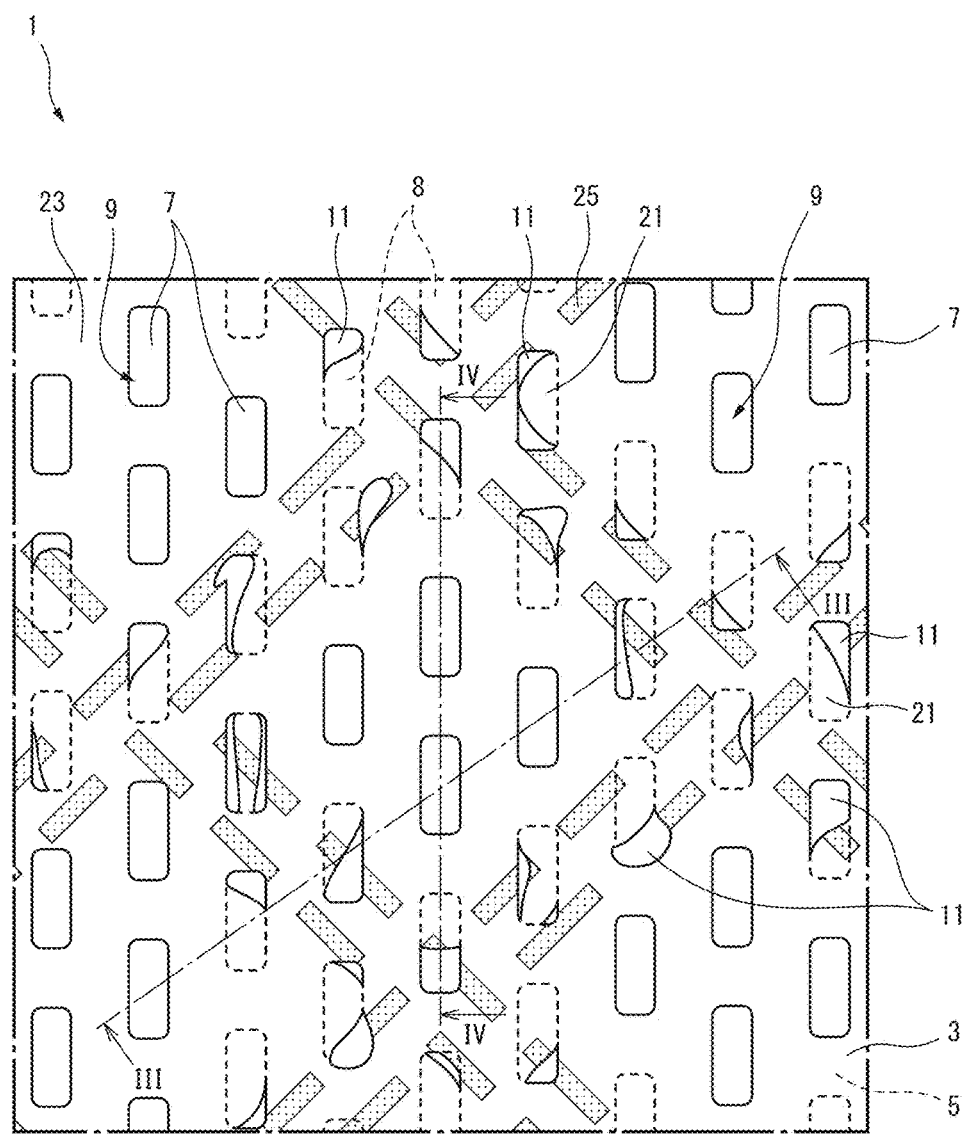
FIG. 2 is an enlarged view of the region II in FIG. 1.
Figure 3:
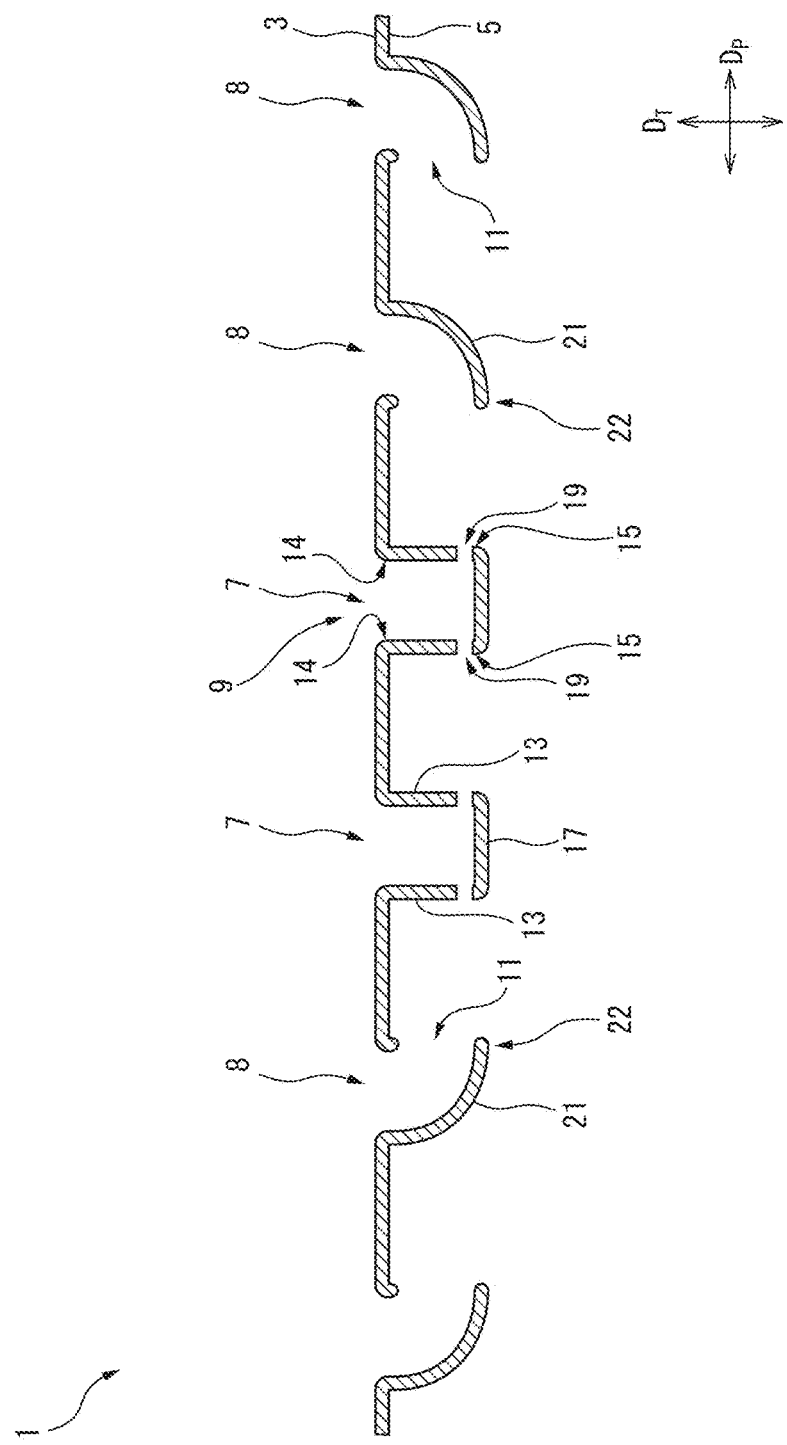
FIG. 3 is an end surface view taken along the end surface in FIG. 2.
Figure 4:
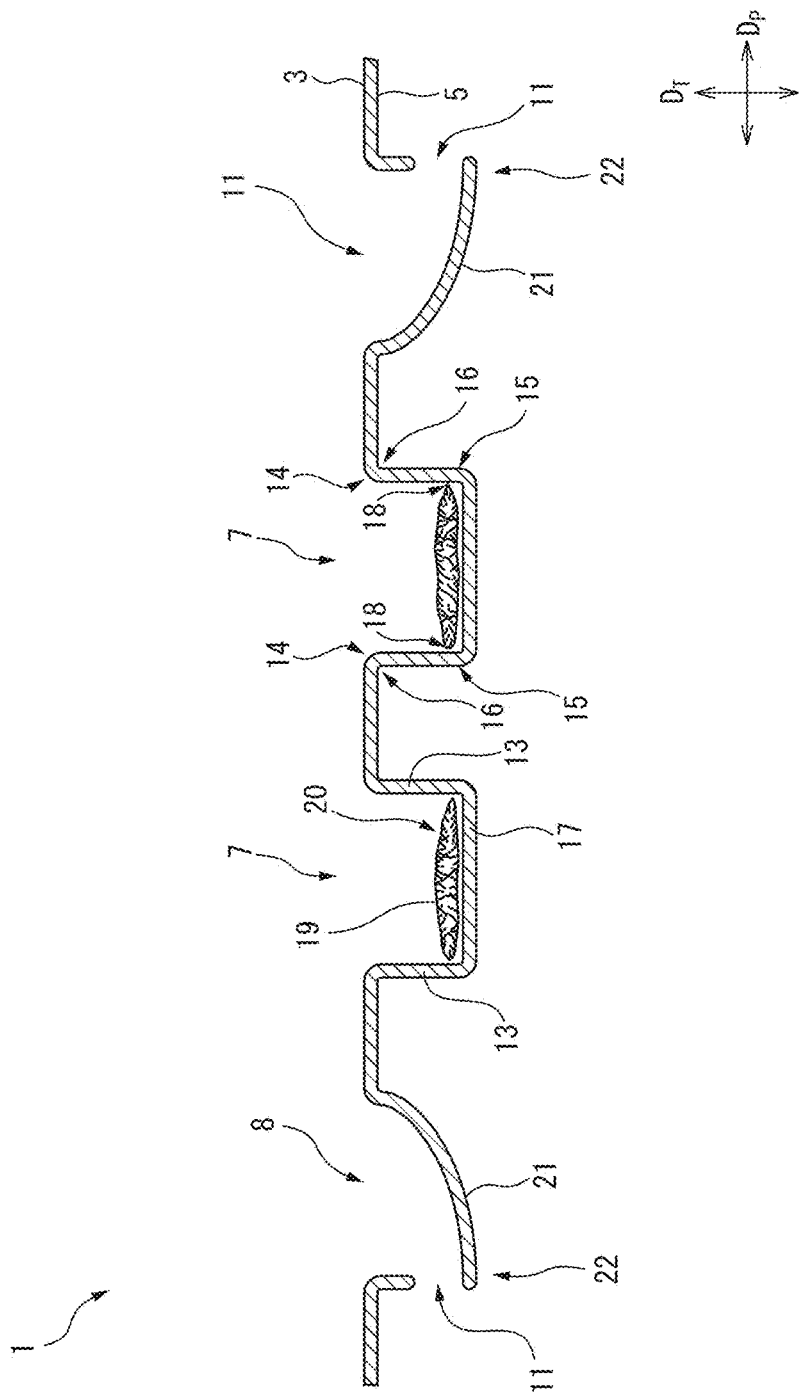
FIG. 4 is an end surface view taken along IV-IV end surface in FIG. 2.

FIGS. 1 to 4 are the drawings so as to explain the shaped nonwoven fabric 1 for an absorbent article, according to one embodiment of the present disclosure (hereinbelow, referred to as the first embodiment). FIG. 1 is a planar view of the shaped nonwoven fabric 1 according to the first embodiment FIG. 2 is an enlarged view of the region II in FIG. 1. FIG. 3 is an end surface view taken along the end surface in FIG. 2. FIG. 4 is an end surface view taken along IV-IV end surface in FIG. 2.

Incidentally, in FIG. 1, penetration holes are not shown from the viewpoint of ease of view. Further, although FIG. 4 is an end surface view, the hole portion 19 formed in the circumferential wall portion 13 of the recessed portion 7, which is disposed in the back, is shown for explanatory purposes.

As shown in FIG. 1, the shaped nonwoven fabric 1 according to the first embodiment includes the first surface 3, the second surface 5 which is positioned on an opposite side of the first surface 3, and a thickness direction (which is not shown). Further, the shaped nonwoven fabric 1 is a nonwoven fabric which is to be used in a state in which the second surface 5 faces the configuration member of the absorbent article. The shaped nonwoven fabric 1 includes the plurality of recessed portions 7 each having the aperture portion 9 on the first surface 3 and each being dented toward the second surface 5 side, and a plurality of second recessed portions 8 each having a penetration hole 11 being provided in the region other than the recessed portions 7 and penetrating through from the first surface 3 to the second surface 5, which are dented toward the second surface 5 side.

Incidentally, in the present description, the plurality of recessed portions each having the aperture portion on the first surface and each being dented toward the second surface side may be referred to as the first recessed portions, in order to be distinguished from the second recessed potions.

Further, in FIGS. 1 and 2, in order to distinguish between the first recessed portions 7 and the second recessed portions 8, the first recessed portions 7 are expressed by the solid lines, and the second recessed portions 8 are expressed by the broken lines.

Each of the first recessed portions 7 includes the circumferential wall portion 13 which extends in the thickness direction of the shaped nonwoven fabric 1 from the edge 14 of the aperture portion 9 toward the second surface 5 side, the edge 15 positioned on the opposite side of the aperture portion 9 of the circumferential wall portion 13, and the bottom portion 17 which is provided by being connected to the edge 15 of the circumferential wall portion 13. Further, the circumferential wall portion 13 of each of the first recessed portions 7 includes the hole portion 19 which penetrates through the circumferential wall portion 13 from the first surface 3 to the second surface 5.

Incidentally, the entirety of the edge 16 on the aperture portion 9 side of the circumferential wall portion 13 is connected to the entirety of the edge 14 of the aperture portion 9, and the entirety of the edge 15 on the bottom portion 17 side of the circumferential wall portion 13 is connected to the entirety of the edge 18 of the bottom portion 17.

The shaped nonwoven fabric 1 includes the plurality of first recessed portions 7 each being dented toward the second surface 5 side, and the circumferential wall portion 13 of each of the first recessed portions 7 includes the hole portion 19. Accordingly, the first recessed portions 7 have improved softness, and the shaped nonwoven fabric 1 has an improved texture of the first surface 3.

Further, the shaped nonwoven fabric 1 includes the plurality of first recessed portions 7 each being dented toward the second surface 5 side, whereby on the second surface 5 side, the region 23 other than the recessed portions form the ventilation passage in the planar direction, and thus the shaped nonwoven fabric is superior in the air permeability in the planar direction $D_P$. Further, the shaped nonwoven fabric 1 includes the plurality of penetration holes 11 and the hole portion 19 which is formed in at least a part of the circumferential wall portion 13 of the plurality of first recessed portions 7, and these form the ventilation passage in the thickness direction $D_T$ which communicates with the ventilation passage in the planar direction $D_P$, whereby the shaped nonwoven fabric 1 is superior in the air permeability in the thickness direction $D_T$ due to ease of the air on the second surface 5 side moving to the first surface 3 side.

In each of the second recessed portions 8, the partially ruptured portion 21 which is formed by a part of the shaped nonwoven fabric 1 is dented toward the second surface 5 side, and as a result, the penetration hole 11 is formed in between the partially ruptured portion 21 and the remaining portion of the shaped nonwoven fabric 1. Incidentally, a part of the partially ruptured portion 21 is connected to the shaped nonwoven fabric 1. The penetration hole 11 penetrates through in the substantially horizontal direction in each of the second recessed portions 8.

In the penetration hole 11, the end portion 22 of the partially ruptured portion 21 includes a part of the fusion portion 25.

In the shaped nonwoven fabric 1, the partially ruptured portion 21 which is formed by a part of the shaped nonwoven fabric 1 is dented toward the second surface 5 side of the shaped nonwoven fabric 1, whereby the penetration hole 11 is formed. As a result, the ventilation passage in the planar direction $D_P$ and the ventilation passage in the thickness direction $D_T$ are reliably connected. Further, the partially ruptured portion 21 is dented toward the second surface 5 side, whereby the shaped nonwoven fabric 1 is superior in the texture of the first surface 3.

The shaped nonwoven fabric 1 includes a thermoplastic resin fiber, and the shaped nonwoven fabric 1 includes the plurality of fusion portions 25 in which the thermoplastic resin fiber is fused, in the region 23 other than the recessed portions. Further, at least in a part of the plurality of penetration holes 11, the end portion 22 of the partially ruptured portion 21 includes a part of the plurality of fusion portions 25.

According to this configuration, it becomes difficult for the end portion 22 of the partially ruptured portion 21 to be fuzzy, whereby the first surface 3 is superior in the texture.

The shaped nonwoven fabric 1 includes the plurality of fusion regions 27 which is formed by being intermittently disposed with the plurality of fusion port ions 25 in the direction parallel to the first direction $D_1$, and the plurality of fusion regions 28 which is formed by being intermittently disposed with the plurality of fusion portions 25 in the second direction $D_1$ that is the direction orthogonal to the first direction $D_1$. Each of the plurality of fusion regions 27 extends in the direction parallel to the first direction $D_1$, and a plurality of sets each consisting of two fusion regions 27 are disposed in the second direction $D_2$ with a predetermined interval W. In the same manner, each of the plurality of fusion regions 28 extends in the direction parallel to the second direction $D_2$, and a plurality of sets each consisting of two fusion regions 28 are disposed in the first direction $D_1$ with a predetermined interval W.

Further, the shaped nonwoven fabric 1 includes the compartmented region 29 which is compartmented by two fusion regions 27 that is disposed with the interval W, and two fusion regions 28 that is disposed with the interval W, and further includes a plurality of, for example, three to five first recessed portions 7 on the inside of the compartmented region 29.

According to this configuration, the ventilation passage in the planar direction $D_P$ is secured by the first recessed portions 7, and the ventilation passage in the thickness direction $D_T$ is secured by the second recessed portions 9 formed on the compartmented region 29 and by the penetration hole 11, whereby it becomes easier for the air on the second surface 5 side to move to the first surface 3 side.

The hole portion 19 which is formed in the circumferential wall portion 13 includes the peripheral portion 20 which is formed without being fused with the thermoplastic resin fiber. Accordingly, the shaped nonwoven fabric 1 has an improved texture of the first surface 3.

Each of the plurality of first recessed portions 7 if includes a substantially rectangular parallelepiped space with an upper opening which has a substantially rectangular aperture portion 9 in planar view, a circumferential wall portion 13 and a bottom portion 17. Each of the plurality of first recessed portions 7 protrudes toward the second surface 5 side of the shaped nonwoven fabric 1, and is mutually independent from the other first recessed portions 7.

In the circumferential wall portion 13, the hole portion 19 which penetrates through the circumferential wall portion 13 and communicates from the first surface 3 to the second surface 5 of the shaped nonwoven fabric 1 is formed. The hole portion 19 is formed at the position closer to the bottom portion 17 in the circumferential wall portion 13.

The hole portion 19 includes an internal space which is formed by rupturing the thermoplastic resin fiber without fusing the thermoplastic resin fiber included in the shaped nonwoven fabric 1.

To be more specific, the internal space of the hole portion 19 includes a ruptured end portion of a ruptured thermoplastic resin fiber which includes the ruptured end portion formed by rupturing, among the thermoplastic resin fibers of the shaped nonwoven fabric 1. Accordingly, the internal space of the hole portion 19, the portion cured by the fusion of the thermoplastic resin fiber is not present, and the internal space is formed by a part of the soft thermoplastic resin fiber, or a ruptured thermoplastic resin fiber which has the ruptured end portion formed by rupturing among the thermoplastic resin fibers. Consequently, even when the skin of a user touches the internal space of the hole portion 19, the thermoplastic resin fiber cured by fusion is not present, whereby it is difficult for the user to feel the stiffness and roughness of the nonwoven fabric.

The ruptured thermoplastic resin fiber described here is a fiber which is a part of the thermoplastic resin fibers that form the circumferential wall portion 13, and includes the ruptured end portion which is formed by rupturing the thermoplastic resin fibers, for example, by pulling the same in the length direction or by physically cutting the same.

Accordingly, the fiber diameter of the ruptured end portion is rot increased by the end portion of the fiber being fused and rounded, as in the case in which the thermoplastic resin fiber is fused, and is tapered by tearing, or the changes in the fiber diameter hardly occur. Consequently, even when the skin of a user touches the internal space of the hole portion 19, it is difficult for the user to feel discomfort, etc., due to the stiffness and being caught by the fibers.

In the internal space of the hole portion 19, a part of the thermoplastic resin fibers among the thermoplastic resin fibers is bridged. Further, a part of the ruptured thermoplastic resin fiber is in a state in which the ruptured end portion stretches out to the internal space of the hole portion 19.

Accordingly, the internal space of the hole portion 19 is in a state in which the thermoplastic resin fibers bridged in the internal space and the part of the stretching fibers are mixed, and is not a space which is completely opened.

The shaped nonwoven fabric 1 includes the hole portion 19 which has the internal space and is formed without being fused with the thermoplastic resin fiber, in the circumferential wall portion 13 of the first recessed portions 7. Accordingly, the degree of freedom for the fibers of the shaped nonwoven fabric 1 to move increases, whereby when the shaped nonwoven fabric 1 is pressed in the thickness direction, softness can be felt, and when the skin is slid in the planar direction of the nonwoven fabric, smoothness can be felt.

The hole portion 19 of the first recessed portions 7 includes the internal space which is formed by not fusing the fibers, and the internal space includes the ruptured end portion of the ruptured thermoplastic resin fibers formed by rupturing, and does not include portions cured by fusion. Accordingly, the shaped nonwoven fabric 1 has an excellent stiffness-softness feeling (the softness in the thickness direction) and an excellent roughness-smoothness feeling (the smoothness in the planar direction), and gives a soft feeling to the skin.

The shaped nonwoven fabric of the present disclosure has a height of each of the recessed portions preferably of 0.05 to 2.0 mm, more preferably of 0.075 to 1.5 mm, and even more preferably of 0.1 to 1.0 mm. When the above described height is less than 0.05 mm, it becomes difficult to secure the rigidity of the bottom portion, and there is a tendency that the strength of the shaped nonwoven fabric in the thickness direction is insufficient. When the above described height is more than 2.0 mm, there is a tendency that the strength of the shaped nonwoven fabric in the thickness direction decreases.

The shaped nonwoven fabric of the present disclosure has a long diameter of each of the recessed portions preferably of 0.25 to 5.0 mm, more preferably of 0.5 to 3.0 mm, and even more preferably of 0.75 to 2.0 mm. The ranges are set from the viewpoint of the effects.

In a case in which the shaped nonwoven fabric of the present disclosure has the hole portion in the circumferential wall portion of the recessed portions, the shaped nonwoven fabric has a long diameter of the hole portion preferably of 0.25 to 5.0 mm, more preferably of 0.5 to 3.0 mm, and even more preferably of 0.75 to 2.0 mm. When the above described long diameter is less than 0.25 mm, there may be a case in which the softness of the recessed portions is insufficient, and there may also be a case in which the texture of the shaped nonwoven fabric is decreased. When the above described long diameter is more than 5.0 mm, the hole portion is large, and it becomes easier for the peripheral portion thereof to be fuzzy, whereby there may be a case in which the texture of the shaped nonwoven fabric is decreased.

In the same manner, in the case in which the shaped nonwoven fabric of the present disclosure has the hole portion in the circumferential wall port ion of the recessed portions, the shaped nonwoven fabric has a length of the hole portion in the thickness direction preferably of 0.1 to 5.0 mm, more preferably of 0.25 to 3.0 mm, and even more preferably of 0.5 to 2.0 mm. When the above described length in the thickness direction is less than 0.1 mm, there may be a case in which the softness of the recessed portions cannot be secured, and the texture of the shaped nonwoven fabric is decreased. When the above described length in the thickness direction is more than 5.0 mm, it becomes easier for the peripheral portion of the hole portion to be fuzzy, and there may be a case in which the texture of the shaped nonwoven fabric is decreased.

In the case in which the shaped nonwoven fabric of the present disclosure has the hole portion in the circumferential wall portion of the recessed portions, the hole portion is preferably provided at the position closer to the bottom portion in the circumferential wall portion of the recessed portions. This is for the purpose of placing the hole portion as far as possible from the first surface of the shaped nonwoven fabric, whereby of reducing the opportunity for the hole portion to come in contact with the skin, and of making it difficult to feel discomfort and foreign-body sensation.

Accordingly, the smoothness when the skin is slid in the planar direction of the nonwoven fabric can be more secured.

In the case in which the shaped nonwoven fabric of the present disclosure has the hole portion in the circumferential wall portion of the recessed portions, a part of the thermoplastic resin fibers is preferably bridged in the internal space of the hole portion. Even in a case in which the skin of the user comes in contact with the hole portion, the difference in the feeling of the circumferential wall portion and the bottom portion of the recessed portions is to be smaller by the thermoplastic resin fibers bridged in the internal space, whereby it becomes difficult for the user to feel discomfort. That is, the thermoplastic resin fibers bridged in the internal space of the hole portion do not penetrate completely through the hole portion and do not reach the second surface of the shaped nonwoven fabric, whereby the level difference at the boundary of the circumferential wall portion and the bottom portion, and the hole portion is to be smaller on tactile basis. Accordingly, the texture becomes relatively smooth, and it becomes difficult for the user to feel discomfort.

In the case in which the shaped nonwoven fabric of the present disclosure has the hole portion in the circumferential wall portion of the recessed portions, the hole portion has an aperture ratio of the internal space preferably of 1 to 50%, more preferably of 1.5 to 35%, and even more preferably of 2.5 to 20%. When the above described aperture ratio is less than 1%, the aperture ratio is low, and there is a tendency that the shaped nonwoven fabric is inferior in the texture. When the above described aperture ratio is 50% or more, it becomes easier for the strength of the circumferential wall portion provided in the hole portion to be lowered, and further, there is a possibility that the boundary of the peripheral portion of the hole portion is more easily detected on tactile basis.

The nonwoven fabric to be shaped of the present disclosure has the basis weight normally of 10 to 100 m$^2$, preferably of 15 to 75 g/m$^2$, and more preferably of 20 to 50 g/m$^2$. Further, the nonwoven fabric to be shaped has the thickness normally of 0.1 to 4.0 mm, preferably of 0.3 to 3.0 mm, and more preferably of 0.5 to 2.0 mm.

In the present description, the thickness (mm) of the nonwoven fabric is measured in the following manner.

FS-60DS [the measurement surface of 44 mm (in diameter), the measurement pressure of 3 g/cm$^2$] manufactured by Daiei Kagaku Seiki MFG. Co., Ltd. is prepared, five different portions of the nonwoven fabric is applied with pressure under the standard condition (the temperature of 23±2° C., the relative humidity of 50±5%), the thickness of each of the portions ten seconds after the pressure is applied is measured, and the average value of the five measurement values is to be the thickness of the nonwoven fabric.

Further, the first embodiment, a part of the thermoplastic resin fibers among the thermoplastic resin fibers is bridged in the internal space of the hole portion 19, however, in the nonwoven fabric according another embodiment of the present disclosure, fibers bridged in the intern space of the hole portion may not be present.

In the first embodiment, each of the first recessed portions 7 is formed in the substantially rectangular parallelepiped shape; however, in the nonwoven fabric the present disclosure, the shape of the recessed portions may be arbitrary, and for example, a columnar shape, a prismatic, shape may be cited.

In the nonwoven fabric of the present disclosure, the fiber density of the bottom portion of the recessed portions in the shaped nonwoven fabric is preferably higher than the fiber density of the portions other than the recessed portions. This is because such shaped nonwoven fabric is superior in the rigidity.

Further, in the nonwoven fabric of the present disclosure, the thermoplastic resin fibers are preferably not fused in the bottom portion of the recessed portions. This is from the viewpoint of the texture.

<The Absorbent Article>

Next, the absorbent article of the present disclosure is described.

The absorbent article according to one embodiment of the present disclosure (which is the second embodiment) includes a liquid permeable sheet, a liquid impermeable sheet, and an absorbent body positioned therebetween. Further, the liquid permeable sheet is the above described shaped nonwoven fabric, and the second surface thereof faces the absorbent body.

According to this configuration, the ventilation passage in the planar direction is formed in between the second surface of the shaped nonwoven fabric and the materials of the absorbent article, and in the region other than the recessed portions, whereby the air with high humidity inside the absorbent article can move in the planar direction of the shaped nonwoven fabric in between the shaped nonwoven fabric and the materials by passing through the ventilation passage in the planar direction. Further, the air with high humidity which has moved in the planar direction can move to the outside of the absorbent article by passing through the hole portion and the penetration hole which are the ventilation passage in the thickness direction.

Incidentally, the second surface of the shaped nonwoven fabric is not required to be directly joined to the absorbent body, as long as the second surface thereof faces the absorbent body. For example, in a case of an absorbent article which includes a liquid permeable sheet, an auxiliary sheet such as a diffusion sheet, etc., an absorbent body, and a liquid impermeable sheet, in this order, the second surface of the above described shaped nonwoven fabric as the liquid permeable sheet faces the absorbent body, and is joined to the auxiliary sheet.

An absorbent article according to another embodiment of the present disclosure (which is the third embodiment) includes a liquid permeable sheet, a liquid impermeable sheet, an absorbent body positioned therebetween, and an exterior sheet disposed on a surface of the liquid impermeable sheet that is on an opposite side of the absorbent body. Further, the exterior sheet is the above described nonwoven fabric according, and the second surface thereof faces the liquid impermeable sheet.

According to this configuration, the absorbent article is superior in the texture.

Incidentally, the second surface of the shaped nonwoven fabric is not required to be directly joined to the liquid impermeable sheet, as long as the second surface thereof faces the liquid impermeable sheet. For example, in a case of an absorbent article which includes a liquid permeable sheet, an absorbent body, a liquid impermeable sheet, an auxiliary sheet, and an exterior sheet, in this order, the second surface of the above described shaped nonwoven fabric as the exterior sheet faces the liquid impermeable sheet, and is joined to the auxiliary sheet.

<The Manufacturing Method of the Shaped Nonwoven Fabric>

Next, the manufacturing method of the shaped nonwoven fabric of the present disclosure (hereinbelow, which may be referred to as "the method of the present disclosure") is described.

The method of the present disclosure includes the following steps:
(1) the preheating step of preheating the nonwoven fabric to be shaped which includes the first surface and the second surface, and further includes the thermoplastic resin fiber (hereinbelow, which may be referred to as "the preheating step"),
(2) a step of forming a shaped nonwoven fabric by making the preheated nonwoven fabric to be shaped pass through between a pair of shaping members which include a first shaping member and a second shaping member so that the first surface and the second surface come in contact with the second shaping member and the first shaping member, respectively, and so as to shape the nonwoven fabric to be shaped (hereinbelow, which may be referred to as "the shaping step").

Incidentally, in the pair of shaping members, the first shaping member includes a plurality of ridges which extend in one direction and a plurality of grooves each being disposed between the plurality of ridges, and the second shaping member includes a plurality of pins each of which having a tip portion that is disposed intermittently along the one direction and is disposed so as to engage with each of the plurality of grooves.

The manufacturing method of the shaped nonwoven fabric according to one embodiment of the present disclosure (which is the fourth embodiment) is described with reference to FIGS. 5 to 9. Incidentally, as for the shaped nonwoven fabric which is manufactured by the above described manufacturing method, the shaped nonwoven fabric 1 in accordance with the first embodiment as shown in FIGS. 1 to 4 should be referred to.

Figure 5:
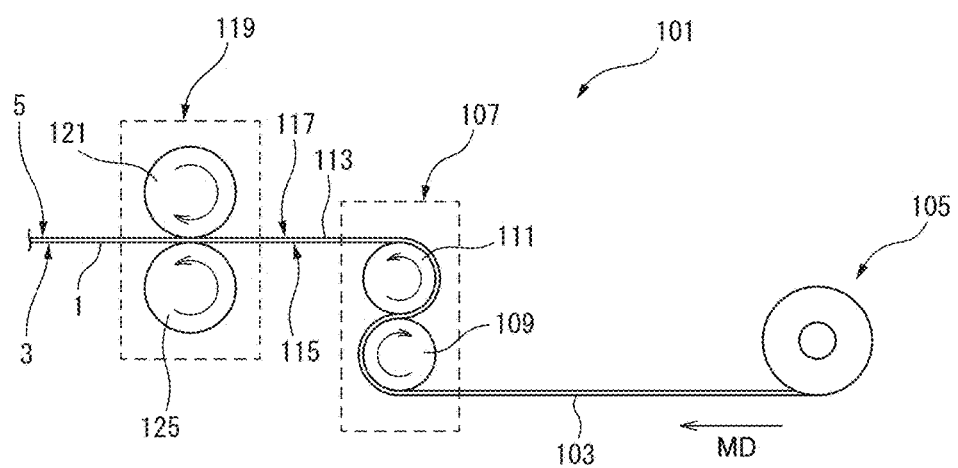
FIG. 5 is a schematic view of the manufacturing apparatus 101 which is used in the method according to the fourth embodiment.
Figure 6:
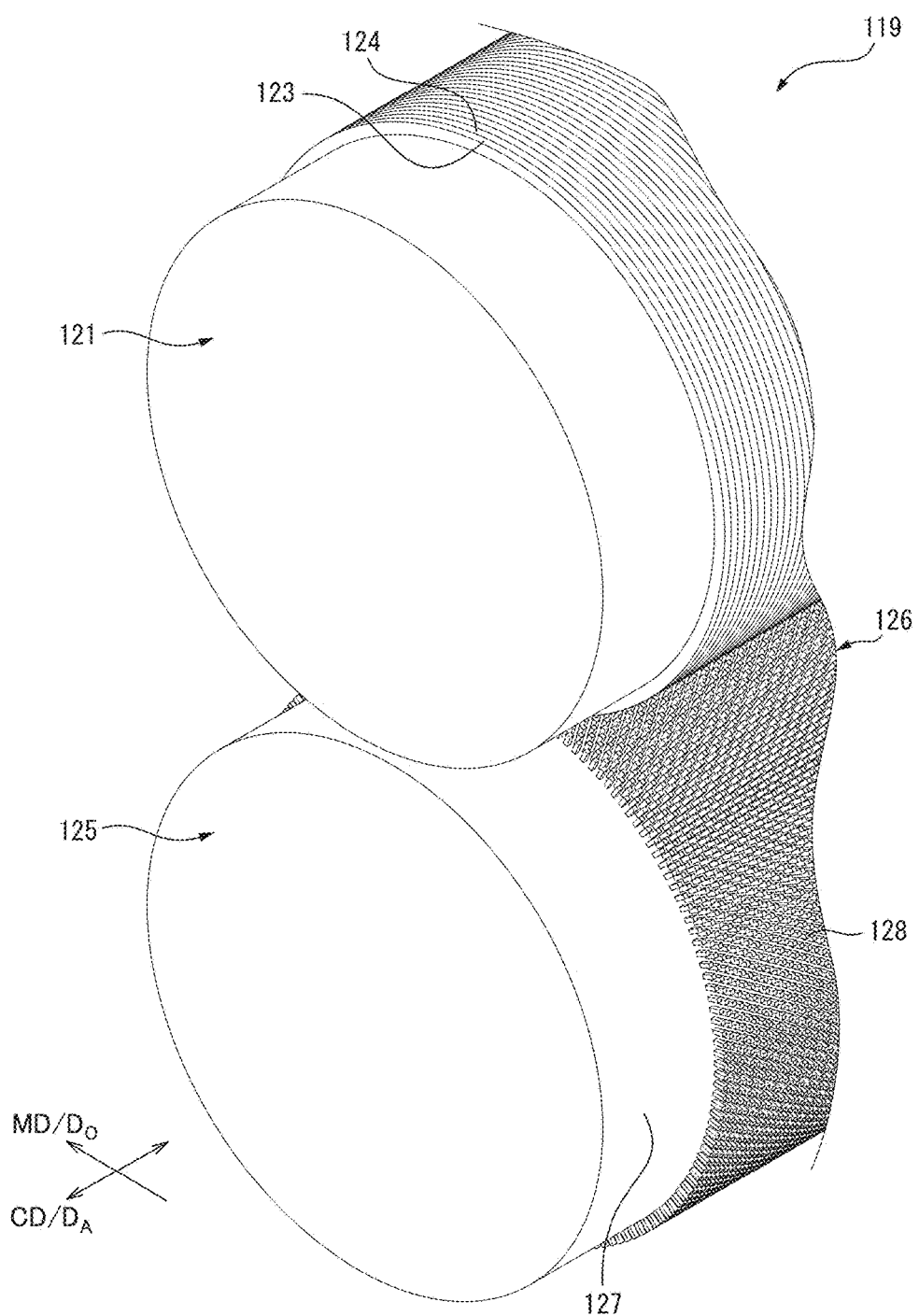
FIG. 6 is an enlarged perspective view of the main portions schematically showing the first shaping roll 121 and the second shaping roll 125.
Figure 7:
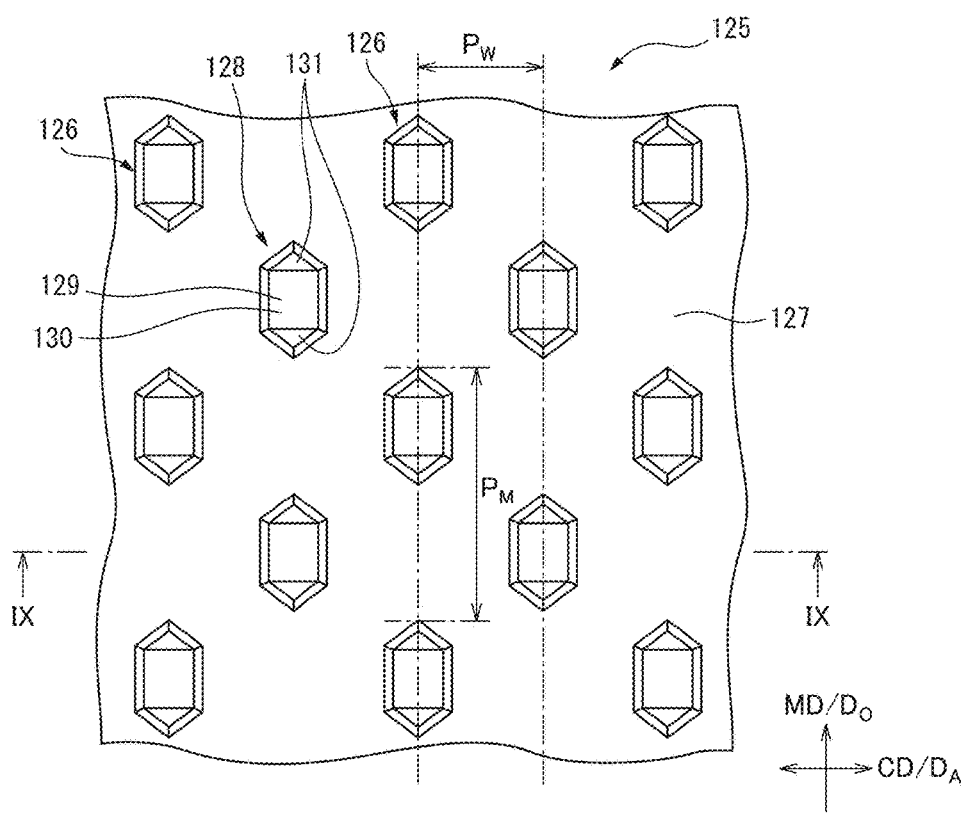
FIG. 7 is an enlarged view of the main portions schematically showing the arrangement of the pin 126 of the second shaping roll 125.

FIG. 5 is a schematic view of the manufacturing apparatus 101 which is used in the method according to the fourth embodiment. FIG. 6 is an enlarged perspective view of the main portions schematically showing the pair of shaping rolls 121 and 125. FIG. 7 is an enlarged view of the main portions schematically showing the arrangement of the pin 126 of the second shaping roll 125. FIG. 8(a) is a perspective view of the pin 126 of the second shaping roll 125, and FIG. 8(b) is a sectional view of the pin 126 of the second shaping roll 125 in the one direction $D_O$ (which is the conveying direction MD). FIG. 9 is an enlarged view of the main portions showing the engagement of the first shaping roll 121 and the second shaping roll 125. FIG. 9 is a sectional view which corresponds to the IX-IX cross section in FIG. 7 at the time of engagement of the first shaping roll 121 and the second shaping roll 125.

In the preheating step, the nonwoven fabric 103 to be shaped which is unwound from the unwinding device 105 and is conveyed in the conveying direction MD is made to be in sequential contact with the outer circumferential surface of the rotating one pair of preheating rolls (which are the first preheating roll 109 and the second preheating roll 111) of the preheating device 107, whereby the preheating is performed.

The shaping step is performed by using the shaping device 119. The shaping device 119 includes one pair of shaping rolls, that is, the first shaping roll 121 disposed on the upper side, and the second shaping roll 125 disposed on the lower side. As shown in FIG. 6, the first shaping member 121 includes the plurality of ridges 123 which extend in the one direction $D_O$ (which is the conveying direction MD) and the plurality of grooves 124 each being disposed between the plurality of ridges 123, and each extending in the one direction $D_O$ (which is the conveying direction MD), and the second shaping member 125 includes the plurality of pins 126 each of which having a tip portion 128 that is disposed, intermittently along the one direction $D_O$ (which is the conveying direction MD) and is disposed so as to engage with each of the plurality of grooves 124. The plurality of pins 126 are formed on the outer circumferential surface 127 of the second shaping roll 125.

Incidentally, each of the plurality of ridges 123 and each of the plurality of grooves 124 are alternately disposed in the other direction $D_A$ (which is the width direction CD) which is orthogonal to the one direction $D_O$ (which is the conveying direction MD).

As shown in FIGS. 6 and 7, the plurality of pins 126 are arranged intermittently, and more specifically are arranged substantially linearly with the pitch $P_M$, in the one direction $D_O$ (which is the conveying direction MD, and the circumferential direction of the second shaping roll 125). The plurality of pins 126 are also arranged with the pitch $P_W$ so as not to come in contact with the ridges 123 of the first shaping roll 121, in the direction $D_A$ (which is the width direction CD, and the width direction of the second shaping roll 125). Further, the plurality of pins 126 are disposed in a staggered manner on the outer circumferential surface 127 of the second shaping roll 125.

Figure 8:
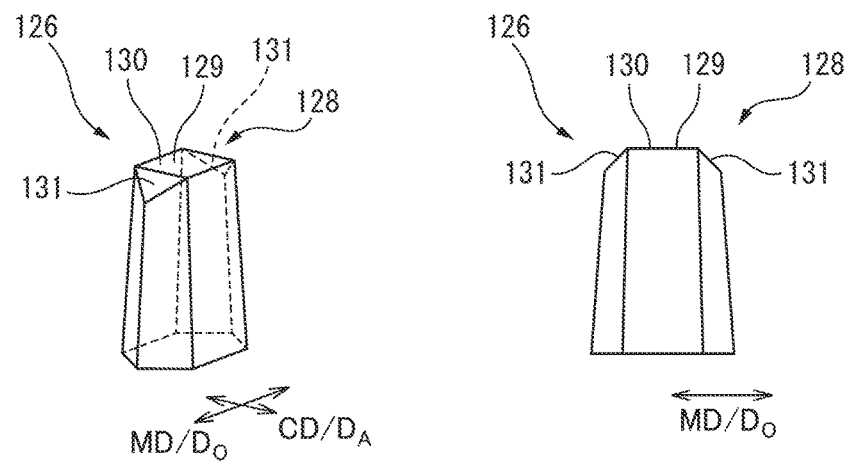
FIG. 8 is a diagram to explain the pin 126 of the second shaping roll 125.
Figure 9:
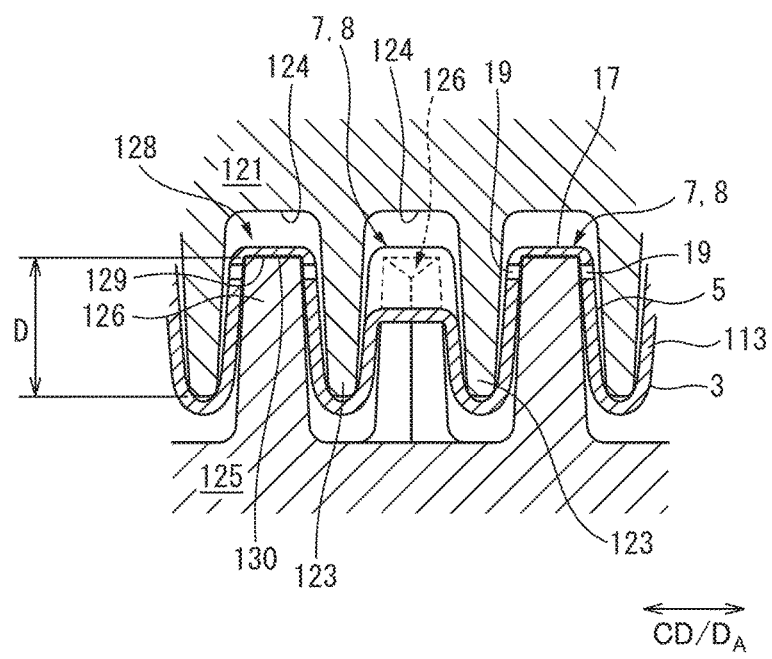
FIG. 9 is an enlarged view of the main portions showing the engagement of the first shaping roll 121 and the second shaping roll 125.

As shown in FIGS. 7 to 9, each of the pins 126 includes a flat surface 130 at the tip 129 of the tip portion 128. The flat surface 130 comes into contact with the first surface 3 of the preheated nonwoven fabric 113 to be shaped so as to be in parallel with the same in the shaping step, and forms the bottom portion 17 of the first recessed portions 7 in the shaped nonwoven fabric. Each of the pins 126 further includes one pair of tapered surfaces 131 and 131 which are adjacent in the one direction $D_O$ with the flat surface 130 positioned therebetween at the tip portion 128. Each of the pair of tapered surfaces 131 and 131 is disposed with an angle so that the tip portion 128 is tapered toward the tip 129 in the one direction $D_O$.

Further, each of the pair of tapered surfaces 131 and 131 has a substantially triangular shape, and is formed so that the width thereof becomes smaller as each of the pair of tapered surfaces 131 and 131 becomes distant from the flat surface 130.

In the shaping step, the preheated nonwoven fabric 113 which is to be shaped is made to pass through between the first shaping roll 121 and the second shaping roll 125 which rotate in a state of being engaged in the shaping device 119, and the preheated nonwoven fabric 113 which is to be shaped is stretched in between the ridges 123 and grooves 124 of the first shaping roll 121 disposed on the upper side and the pins 126 of the second shaping roll 125 disposed on the lower side, which are engaged with each other, whereby the preheated nonwoven fabric 113 which is to be shaped is shaped.

Incidentally, when performing the shaping step, the first shaping roll 121 and the second shaping roll 125 are preferably heated so that it becomes easier for the preheated nonwoven fabric 113 which to be shaped, to be shaped.

The first shaping roll 121 disposed on the upper side makes the ridges 123 come in contact with the second surface 5 of the preheated nonwoven fabric 113 which is to be shaped, and pushes the portions which are in contact in the direction of the second shaping roll 125 disposed on the lower side.

The second shaping roll 125 disposed on the lower side makes the plurality of pins 126 aligned in the one direction $D_O$ (which is the conveying direction MD) come in contact with the first surface 3 of the preheated nonwoven fabric 113 which is to be shaped, and pushes the portions which are in contact with the tip portion 128 of the pins 126 into the inside of the grooves 124 of the first shaping roll 121 disposed on the upper side.

As a result, in the region in which the fusion portions 25 are not present in the preheated nonwoven fabric 113 which is to be shaped, the portions which have been in contact with the tip portion 128 of the pins 126 are pushed strongly into the inside of the grooves 124 to be shaped, whereby the first recessed portions 7 each having the bottom portion 7 are formed. On the other hand, in the region in which the fusion portions 25 are present in the preheated nonwoven fabric 113 which is to be shaped, the portions which have been in contact with the tip portion 128 of the pins 126 are pushed strongly into the inside of the grooves 124, whereby the partially ruptured portions 21 which are formed by a part of the shaped nonwoven fabric 1, and a part of which is connected to the shaped nonwoven fabric 1, are formed.

Incidentally, the bottom portion 17 of the first recessed portions 7 is formed at the time of shaping, by the tip portion 128 of the pins 126, and more specifically the flat surface 130 at the tip 129 of the tip portion 128, pushing the abutting portions of the preheated nonwoven fabric 113 which is to be shaped, into the inside of the grooves 124, in a state in which the first shaping roll 121 disposed on the upper side and the second shaping roll 125 disposed on the lower side engaging with the preheated nonwoven fabric 113 which is to be shaped. Accordingly, the bottom portion 17 has a higher fiber density than the other portions, for example, the portions other than the first recessed portions 7 and which are the portions other than the fusion portions 25, and is superior in the rigidity. Consequently, the shaped nonwoven fabric 1 is superior in the rigidity due to the bottom portion 17 of the first recessed portions 7.

In the preheated nonwoven fabric 113 which is to be shaped, the portions which have been in contact with the both end portions in the other direction (the width direction CD) of the tip portion 128 of the pins 126, rupture the thermoplastic resin fibers, whereby form the ruptured thermoplastic resin fibers which include ruptured end portions, by the tensile force, etc., which is generated when the ridges 123 push the nonwoven fabric 103 to be shaped in the direction of the second shaping roll 125 disposed on the lower side, and when the pins 126 push the nonwoven fabric 103 to be shaped in the direction of the first shaping roll 121 disposed on the upper side.

As a result, the hole portion 19 which includes the ruptured end portion of the ruptured thermoplastic resin fibers is formed in the first recessed portions 7. Incidentally, a part of the thermoplastic resin fibers remains in the internal space of the hole portion 19 in the state of being bridged, and a part of the ruptured end portions of the ruptured thermoplastic resin fibers is in a state of being stretched out to the internal space. The hole portion 19 is formed in the circumferential wall portion 13.

In the method of the present disclosure, the means to preheat the nonwoven fabric to be shaped in the preheating step is not particularly limited, and for example, as in the fourth embodiment, the nonwoven fabric to be shaped may be wrapped around the preheating members, and more specifically, the preheating rolls, whereby the nonwoven fabric to be shaped may be preheated. Further, the nonwoven fabric to be shaped may alternatively be blown with a heated fluid, for example, a heated air, whereby the nonwoven fabric to be shaped may be preheated. In the viewpoint of manufacturing the shaped nonwoven fabric in a high speed, the preheating step is preferably performed by using the preheating members.

In the preheating step, the preheating temperature: $T_P$ (° C.) of the preheating members and the heated fluid has a relationship with the melting point: $T_M$ (° C.) of the thermoplastic resin fibers which configure the nonwoven fabric to be shaped preferably of $T_M-80<T_P<T_M-20$, more preferably of $T_M-70<T_P<T_M-25$, and even more preferably of $T_M-60<T_P<T_M-30$. This relationship is preferable from the viewpoint of performing the shaping in a high speed in the subsequent shaping step. From the viewpoint of performing the shaping step in a high speed, the preheating temperature is preferably closer to the melting point of the thermoplastic resin fibers; however, if the preheating temperature is too high, the thermoplastic resin fibers are fused with each other, and there is a tendency that the shaped nonwoven fabric becomes stiff, and in the subsequent shaping step, there may be a case in which the shapes of the ridges and the grooves of the first shaping member are shaped.

Incidentally, in a case in which the thermoplastic resin fiber, etc., includes a plurality of types of thermoplastic resins, for example, in a case of a composite fiber, the above described melting point means the melting point of the thermoplastic resin of the lower or the lowest melting point among the plurality of types of thermoplastic resins.

In the method of the present disclosure, in the shaping step, the shape of each of one pair of the shaping members which shape the preheated nonwoven fabric to be shaped is not particularly limited, as long as the first shaping member includes a plurality of ridges which extend in one direction and a plurality of grooves each being disposed between the plurality of ridges, and the second shaping member includes a plurality of pins each of which being disposed intermittently along the one direction and being disposed so as to engage with each of the plurality of grooves. For example, one pair of the shaping members may include the ridges, the grooves, the pins, etc., in a planar substrate. In a case in which the one pair of the shaping members is one pair of shaping rolls, the shaped nonwoven fabric can be manufactured in a high speed.

In the method of the present disclosure, in the shaping step, the preheated nonwoven fabric to be shaped is preferably heated. This is preferable from the viewpoint of manufacturing the shaped nonwoven fabric in a high speed. In order to heat the preheated nonwoven fabric to be shaped, one of or the both of the first shaping member and the second shaping member are preferably heated.

From the viewpoint of the above, the first shaping member and/or the second shaping member may be heated to the shaping temperature: $T_S$(° C.), and the shaping temperature: $T_S$(° C.) and the melting point: $T_M$(° C.) of the thermoplastic resin fibers have a relationship preferably of $T_M-80<T_S<T_M-20$, more preferably of $T_M-70<T_S<T_M-25$, and even more preferably of $T_M-60<T_S<T_M-30$.

In the method of the present disclosure, the shaping temperature: $T_S$(° C.) and the preheating temperature: $T_P$(° C.) have a relationship preferably of $-20 \leq T_S-T_P \leq +20$, more preferably of $-10 \leq T_S-T_P \leq +10$, and even more preferably of $-5 \leq T_S-T_P \leq +5$. Accordingly, in the shaping step, the time to adjust the preheated nonwoven fabric to be shaped to the shaping temperature can be reduced, and the shaped nonwoven fabric can be manufactured with a high speed. Incidentally, considering that the temperature of the preheated nonwoven fabric to be shaped may be lowered during the time from the preheating step to the shaping step, the preheating temperature: $T_P$ (° C.) may be set to be higher than the shaping temperature: $T_S$ (° C.).

In the method of the present disclosure, the height of the ridges of the first shaping member (which is the height from the root to the tip of each of the ridges) the may be appropriately set according to the desired performance of the shaped nonwoven fabric; however, from the viewpoint of forming a shaped nonwoven fabric with excellent texture the height of the ridges preferably 0.25 to 5.0 mm, more preferably is 0.5 to 3.0 mm, and even more preferably is 1.0 to 2.5 mm.

In the method of the present disclosure, the depth of engagement between the first shaping member and the second shaping member preferably is 0.5 to 3.0 mm, and more preferably is 1.0 to 2.0 mm. When the depth of engagement is less than 0.5 mm, it becomes more difficult for the recessed portions to be formed in the shaped nonwoven fabric, and when the depth of engagement is more than 3.0 mm, there is a tendency that the strength of the shaped nonwoven fabric decreases.

Incidentally, in the present description, the depth of engagement means the height between the tip of each of the ridges of the first shaping member and the tip of each of the pins of the second shaping member, as shown in symbol D in FIG. 9.

In the method of the present disclosure, each of the plurality of pins preferably includes a flat surface at the tip of the tip portion. This is because, it becomes difficult for the bottom portion of the recessed portions to include a hole portion, and the fiber density of the bottom portion of the recessed portions becomes higher than the fiber density of the portions other than the recessed portions, in the shaped nonwoven fabric, whereby the shaped nonwoven fabric is superior in the rigidity. In such cases, the area of the flat surface may be appropriately set according to the desired performance of the shaped nonwoven fabric; however, from the viewpoint of forming a shaped nonwoven fabric with an excellent texture the flat surface has an area preferably of 0.1 to 1.0 mm$^2$, and more preferably of 0.2 to 0.8 mm$^2$.

In the method of the present disclosure, the tip portion of each of the plurality of pins includes the flat surface and the above described one pair of tapered surfaces. This is because it becomes more difficult for the hole portion to be formed in the circumferential wall portion of the recessed portions in the shaped nonwoven fabric. Further, this is also because, since the one pair of tapered surfaces of the second shaping member push the nonwoven fabric to be shaped in the direction of the first shaping, member, and even in a case in which the step of forming the shaped nonwoven fabric is performed in a high speed, it becomes easier for the recessed portions to be shaped in a desired shape. The above described one pairs of tapered surfaces preferably are adjacent to each other in the one direction with the flat surface positioned therebetween. This is from the viewpoint of not forming the hole portion in the entirety of the circumferential wall portion of the recessed portions.

The angle formed by each of the one pair of tapered surfaces and the flat surface is preferably 30 to 60°, and is more preferably 40 to 50°. This is from the viewpoints of shaping the recessed portions in the desired shape in a high speed, and of not providing the circumferential wall portion of the recessed portions in the direction in which the one pair of tapered surfaces are disposed.

Each of the one pair of tapered surfaces are preferably formed so that the width thereof becomes smaller as each of the pair of tapered surfaces become distant from the flat surface, and for example, has a shape preferably of a substantially triangular shape, a substantially trapezoidal shape, etc. This is from the viewpoint of not forming the hole portion in the circumferential wall portion of the recessed portions in the direction in which the one pair of tapered surfaces are disposed.

In the method of the present disclosure, the shaping is performed by the one pair of shaping members, that is, the first shaping member including a plurality of ridges which extend in one direction and a plurality of grooves each being disposed between the plurality of ridges, and the second shaping member including a plurality of pins each of which having a tip portion that is disposed intermittently along the one direction and is disposed so as to engage with each of the plurality or grooves. The shaped nonwoven fabric is manufactured by using the above described one pair of shaping members, whereby it becomes more difficult for the one pair of shaping members to be worn by the nonwoven fabric to be shaped, and the shaped nonwoven fabric can be manufactured over a long term and in a high speed.

In the method of the present disclosure, the nonwoven fabric to be shaped is not particularly limited as long as the nonwoven fabric to be shaped includes the thermoplastic resin fibers and the fusion portions, and various types of nonwoven fabrics can be used. As examples of the nonwoven fabric to be shaped, for example, an air through nonwoven fabric, a spunbond nonwoven fabric, a point bond nonwoven fabric, a spun lace nonwoven fabric, a needle punch nonwoven fabric, a meltblown nonwoven fabric and the combinations of these types of nonwoven fabrics, for example, a laminated nonwoven fabric of a spunbond nonwoven fabric and a meltblown nonwoven fabric, for example, a spunbond meltblown spunbond nonwoven fabric (SMS) may be cited.

Incidentally, in a case in which the nonwoven fabric to be shaped is a spunbond nonwoven fabric, or a laminated nonwoven fabric of a spunbond nonwoven fabric and a meltblown nonwoven fabric, it is preferable in that the fusion portions in which the thermoplastic resin fibers configuring the spunbond nonwoven fabric are fused, are ruptured in the shaping step, and the shaped nonwoven fabric includes the penetration holes around the above described embossed portions (and preferably, at portions adjacent to the above described embossed portions).

As the above described thermoplastic resin fibers, those commonly used in the present technical field may be cited, for example, monofilaments such as polyethylene (PE), polypropylene (PP), polyethylene terephthalate (PET), etc., or a fiber formed by graft polymers of PE and PP may be cited. From the viewpoint of manufacturing the shaped nonwoven fabric in a high speed, the thermoplastic resin fiber with a low melting point, for example, polypropylene is preferable.

The above described thermoplastic resin fiber may be a filament. In a case in which the thermoplastic resin fiber is a filament, there is a tendency that the number of ends of the thermoplastic resin fiber per unit volume of the shaped nonwoven fabric decreases, and the shaped nonwoven fabric is superior in the texture.

The above described thermoplastic resin fiber may be a crimped fiber. This is because even when the shaped nonwoven fabric is applied with force, it becomes easier for the shaped nonwoven fabric to maintain the shape thereof, and the shaped nonwoven fabric is superior in the air permeability in the planar direction and in the thickness direction.

As the above described composite fibers, composite fibers such as sheath/core type fibers, side/by/side type fibers and island/ocean type fibers may be cited.

The shaped nonwoven fabric manufactured by the method of the present disclosure is used as a top sheet, a leakage preventing wall, etc., or an exterior sheet of a back sheet of an absorbent article such as a disposable diaper, a sanitary napkin, a urine absorbing pad, a panty liner, etc.

EXAMPLE(S)

Example 1

A spunbond nonwoven fabric was prepared as the nonwoven fabric to be shaped. The spunbond nonwoven fabric is formed by a sheath/core type composite fiber (core: PP type copolymer, sheath: PP, fineness: 1.4 dtex), and had a basis weight of 27 g/m$^2$. The spunbond nonwoven fabric included the fusion portions as shown in FIG. 1.

The spunbond nonwoven fabric was made to pass through the manufacturing devices as shown in FIGS. 5 to 8, whereby the shaped nonwoven fabric No. 1 was formed. Incidentally, the temperatures in the preheating step and in the shaping step were both set to 100° C., and the conveying speed was approximately 250 m/min.

Figure 10:
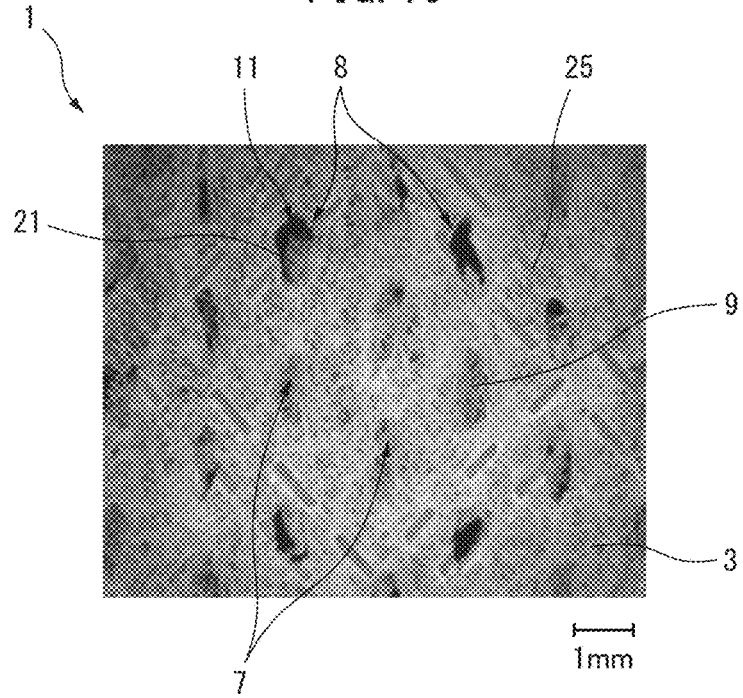
FIG. 10 is an electron microscope picture of the shaped nonwoven fabric No. 1 manufactured in Example 1.
Figure 11:
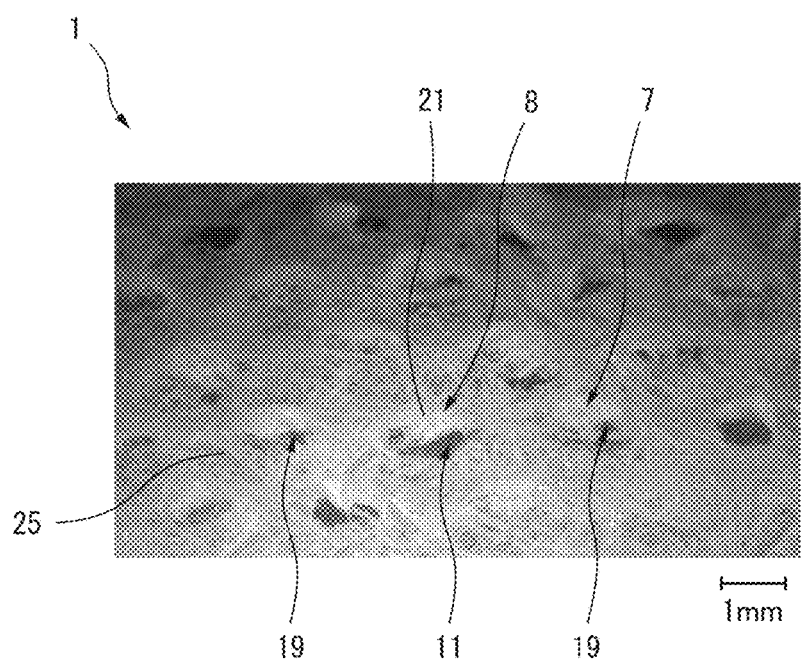
FIG. 11 is an electron microscope picture of the shaped nonwoven fabric No. 1 manufactured in Example 1.

The electron microscope pictures of the shaped nonwoven fabric No. 1 are shown in FIGS. 10 and 11. FIG. 10 is a planar view of the first surface of the shaped nonwoven fabric No. 1, and FIG. 11 is a perspective view of the second surface of the shaped nonwoven fabric No. 1.

REFERENCE SIGNS LIST 1 shaped nonwoven fabric
3 first surface
4 second surface
7 recessed portico (first recessed portion)
8 second recessed portion
9 aperture portion
11 penetration hole
13 circumferential wall portion
14 edge of (aperture portion)
15, 16 edge of (circumferential wall portion)
17 bottom portion
18 edge (of bottom portion)
19 hole portion
20 peripheral portion
21 partially ruptured portion
22 end portion
23 region other than recessed portions
25 fusion portion
27, 28 fusion region
29 compartmented region

The invention claimed is:

1. A nonwoven fabric which is shaped to be used for an absorbent article, including a first surface, a second surface which is positioned on an opposite side of the first surface, and a thickness direction, and being used in a state in which the second surface faces a configuration member of the absorbent article, wherein
the nonwoven fabric includes a thermoplastic resin fiber,
the nonwoven fabric includes a plurality of recessed portions each having an aperture portion on the first surface and each being dented toward a second surface side, and a plurality of penetration holes each being provided in a region other than the recessed portions and each penetrating through from the first surface to the second surface,
each of the plurality of recessed portions includes a circumferential wall portion which extends in the thickness direction from an edge of the aperture portion toward the second surface side, and a bottom portion which is connected to an edge of the circumferential wall portion, the edge of the circumferential wall portion being positioned on an opposite side of the aperture portion,
at least a part of the plurality of recessed portions includes a hole portion which penetrates through the circumferential wall portion from the first surface to the second surface, in the circumferential wall portion
a partially ruptured portion which is formed by a part of the nonwoven fabric and a part of which being connected to the nonwoven fabric, is dented toward the second surface side, in each of the plurality of penetration holes, the nonwoven fabric includes a plurality of fusion portions in which the thermoplastic resin fiber is fused, in the region other than the plurality of recessed portions, and an end portion of the partially ruptured portion includes a part of the plurality of fusion portions, at least in a part of the plurality of penetration holes.

2. The nonwoven fabric according to claim 1, wherein at least one of the plurality of recessed portions is disposed on an inside of a compartmented region which is compartmented by a fusion region in which the plurality of fusion portions are continuously or intermittently disposed.

3. The nonwoven fabric according to claim 1, wherein the hole portion includes a peripheral portion which is formed without being fused with the thermoplastic resin fiber.

4. The nonwoven fabric according to claim 1, wherein the thermoplastic resin fiber includes a filament.

5. The nonwoven fabric according to claim 1, wherein the thermoplastic resin fiber includes a crimped fiber.

6. The nonwoven fabric according to claim 1, wherein the nonwoven fabric is a spunbond nonwoven fabric, or a laminated nonwoven fabric of a spunbond nonwoven fabric and a meltblown nonwoven fabric.

7. The absorbent article which includes a liquid permeable sheet, a liquid impermeable sheet, and an absorbent body positioned between the liquid permeable sheet and the liquid impermeable sheet, wherein the liquid permeable sheet is the nonwoven fabric according to claim 1, and the second surface of the nonwoven fabric faces the absorbent body.

8. The absorbent article which includes a liquid permeable sheet, a liquid impermeable sheet, an absorbent body positioned between the liquid permeable sheet and the liquid impermeable sheet, and an exterior sheet disposed on a surface of the liquid impermeable sheet that is on an opposite side of the absorbent body, wherein the exterior sheet is the nonwoven fabric according to claim 1, and the second surface of the nonwoven fabric faces the liquid impermeable sheet.

9. A manufacturing method of the nonwoven fabric according to claim 1, comprising:

a step of preheating the nonwoven fabric to be shaped which includes the first surface and the second surface, and further includes the thermoplastic resin fiber, and a step of forming a shaped nonwoven fabric by making the preheated nonwoven fabric to be shaped pass through between a pair of shaping members which include a first shaping member and a second shaping member so that the first surface and the second surface come in contact with the second shaping member and the first shaping member, respectively, and so as to shape the nonwoven fabric to be shaped, wherein in the pair of shaping members, the first shaping member includes a plurality of ridges which extend in one direction and a plurality of grooves each being disposed between the plurality of ridges, and the second shaping member includes a plurality of pins each of which having a tip portion that is disposed intermittently along the one direction and is disposed so as to engage with each of the plurality of grooves.

* * * * *